United States Patent [19]

Slaugh

[11] 4,380,657

[45] Apr. 19, 1983

[54] CONVERSION OF ALKANOLS TO ETHERS

[75] Inventor: Lynn H. Slaugh, Houston, Tex.

[73] Assignee: Shell Oil Company, Houston, Tex.

[21] Appl. No.: 355,011

[22] Filed: Mar. 5, 1982

Related U.S. Application Data

[63] Continuation-in-part of Ser. No. 219,279, Dec. 22, 1980, Pat. No. 4,335,022, which is a continuation-in-part of Ser. No. 61,205, Jul. 27, 1979, abandoned.

[51] Int. Cl.$^3$ ............................................. C07D 307/08
[52] U.S. Cl. ..................................... 549/509; 568/698
[58] Field of Search ......................... 549/509; 568/698

[56] References Cited

U.S. PATENT DOCUMENTS 2,251,895   8/1941   Reppe et al. ........................ 549/509

Primary Examiner—Richard Raymond

[57] ABSTRACT

Alkanols are converted to ethers by contact at temperature of 150° C.–550° C. with a novel siliceous composition prepared by impregnating porous silica with aluminum hydride and subsequently heating the impregnated silica to a temperature of from about 300° C. to about 900° C. in a non-oxidizing environment.

14 Claims, No Drawings

CONVERSION OF ALKANOLS TO ETHERS

This application is a continuation-in-part of application Ser. No. 219,279, filed Dec. 22, 1980, now U.S. Pat. No. 4,335,022, which is a continuation-in-part of application Ser. No. 061,205, filed July 27, 1979, now abandoned.

FIELD OF THE INVENTION

This invention relates to a process for converting alkanols to ethers utilizing as catalysts novel siliceous compositions prepared by reacting porous silica with aluminum hydride.

BACKGROUND OF THE INVENTION

Aluminum hydride has been decomposed to produce aluminum metal coatings on glass objects in U.S. Pat. No. 3,501,333, issued Mar. 17, 1970. These processes are typically low temperature processes, below 250° C. The instant compositions contain no aluminum metal.

U.S. Pat. No. 3,146,209, issued Aug. 25, 1964, teaches a method for producing an aluminum hydride containing silica in which bound water molecules on the silica surface are replaced with aluminum hydride molecules to provide a solid composition basically comprising silica and a hydride source attached thereto. There is no teaching in this reference of any subsequent treatment being applied to their gel material to produce an oxide material comparable to the instant compositions.

U.S. Pat. No. 3,305,590, issued Feb. 21, 1967, discloses a general process for making alumino-silicates. This reference generally teaches impregnation of silica with any decomposable aluminum salt. The aluminum hydride used to prepare the instant composition is not considered a salt but rather is a covalent compound (see *Metal Hydrides*, Mueller et al, p. 545, Academic Press, 1968).

SUMMARY OF THE INVENTION

Alkanols are converted to ethers by contacting the alkanols with catalysts comprising unique siliceous materials are prepared by impregnating porous silica with solutions of aluminum hydride and subsequently heating the impregnated silica in a non-oxidizing environment to temperatures of from about 300° to about 900° C. The conversion reaction is typically carried out at temperatures ranging from about 150° C. to about 500° C.

DESCRIPTION OF THE PREFERRED EMBODIMENTS

The porous silicas used in the preparation of the instant composition are readily available commercially and are known as silica gels which are essentially substantially dehydrated amorphorous silica. These materials are available in various density grades, from low density with surface areas ranging from about 100–200 m$^2$/g, to regular density with surface areas up to about 800 m$^2$/g. These commercially available materials are used as desiccants, selective adsorbents, catalysts and catalyst supports. The porous silica may contain minor proportions of other materials without departing from the scope of the invention such as for example alumina and carbon. Prior to use the porous silica should be substantially free of adsorbed water, i.e. "substantially dehydrated". The residuum of chemically bound water, i.e. water of hydration, is not harmful to the process of this invention. The adsorbed or free water is removed by heating the porous silica at temperatures from about 200° to about 900° C. prior to contact with the aluminum hydride impregnating solution. Any environment that will provide for drying is suitable, such as air, vacuum, inert gas such as nitrogen, etc. The dried porous silica should be kept away from a humid atmosphere after drying. A convenient drying atmosphere is that used to heat the impregnated silica, such as nitrogen.

The aluminum hydride suitable for use in preparing the catalysts used in this invention is prepared commercially by reacting at room temperature lithium aluminum hydride and aluminum chloride in diethyl ether (Et$_2$O). The product is isolated in high yield by decanting and drying at room temperature. The product is analyzed as AlH$_3$.1/3Et$_2$O. For purposes of this invention the aluminum hydride is dissolved in a suitable organic solvent. The prime requirement on the solvent is that it be anhydrous and non-hydroxyl containing since water and alcohol react with aluminum hydride. Suitable solvents are for example, ethers, such as diethyl ether, tetrahydrofuran, pyridine, benzene, toluene, chloroform and the like.

To prepare the compositions used in the instant invention, porous silica suitably dried of adsorbed water is contacted with a solution of aluminum hydride in appropriate proportions as to provide the desired amount of aluminum hydride per unit weight of silica. A suitable method of impregnation is described in U.S. Pat. No. 3,146,209, issued Aug. 25, 1964. The impregnated silica is dried of solvent and then heated (activated) in a non-oxidizing atmosphere at temperatures from about 300° C. to about 900° C., more preferably at temperatures of from about 450° C. to about 750° C. The drying step is preferably carried out in the initial stages of the heating step. Suitable non-oxidizing atmospheres are inert atmospheres such as nitrogen, helium, argon, vacuum, etc.; and reducing atmospheres such as hydrogen, carbon monoxide, etc. Drying temperatures are not critical and depend on the particular solvent and will range from about 60 to about 100% of the boiling point (absolute). Drying and heating times are not critical and depend upon temperatures. They are readily determined by simple experimentation. Five minutes to one hour are usually sufficient. Typically the amount of aluminum hydride (measured as aluminum metal) added will range from about 0.01 to about 35, preferably from about 0.1 to about 25 and more preferably from about 1 to about 10 percent by weight of the total composition. Different reactions will require different optimum amounts of aluminum hydride added. For example, for dehydrocoupling of isobutenes to aromatics the aluminum hydride added will range from about 2 to about 10 percent by weight of aluminum per total weight of composition.

The instant compositions find use for catalyzing acid catalyzed reactions. The instant compositions are acidic as compared to the essentially neutral silicas. The instant composition are similar in acidity to the acidic binary alumina-silica gels. While the exact physical structure of the instant composition is not known, it is speculated that the decomposition of the aluminum hydride on the silica surface produces localized Lewis acid sites having an atomic ratio of oxygen to metal ratios lower than the normal oxygen to silica ratio. Analysis of the instant composition indicated no aluminum metal had been deposited on the surface and an insignificant amount of residual aluminum hydride remained. These findings are consistent with the above theory of aluminum hydride reacting with the silica.

The instant compounds prepared using the covalent aluminum hydride compounds differ significantly in their physical characteristic when compared to compounds prepared using decomposable salts. For example, materials prepared using aluminum hydride were compared to those prepared using aluminum nitrate by using X-Ray Photoelectric Spectroscopy (XPS or ESCA). This analysis allowed the relative number of silicon, aluminum and oxygen atoms on the surface to be determined. The composition originating from the $AlH_3$ treatment exhibited a very high ratio of Al/Si atoms on the surface compared to a composition prepared via $Al(NO_3)_3$ wet impregnation. These data suggest concentration of the Al atoms on the external surface when $AlH_3$ is the reactant but not when $Al(NO_3)_3$ is the impregnating material. This concept was confirmed by re-analysis of the compositions after they were ground to expose their interiors. The ratio of Al/Si was substantially less after grinding in the $AlH_3$/$SiO_3$ case but about the same or a little higher in the $Al(NO_3)_3/Al_2O_3$ case. The results are summarized below in Table I.

TABLE 1

Relative Number of Atoms Detected on Surface by XPS (ESCA)

| Sample Treatment | $AlH_3/SiO_2$[b] | | $Al(NO_3)_3/SiO_2$[b] | |
|---|---|---|---|---|
| | 20–30 Mesh Particles | Ground[a] to Powder | 20–30 Mesh Particles | Ground[a] to Powder |
| Si[c] | 100 | 100 | 100 | 100 |
| Al | 25 | 9.9 | 5.0 | 6.5 |
| O | 184 | 164 | 168 | 164 |

[a]Ground to a fine powder in Argon.
[b]Impregnated materials were activated in a stream of $N_2$ in 50° stages to 700° C. The aluminum content of the final product was about 3.8-4% wt. Davison 57 grade $SiO_2$ was employed as the support.
[c]Data normalized to Si = 100.

The alkanols utilized in the instant process typically have carbon numbers ranging from one to about thirty, preferably from 1 to about 20, and more preferably from one to about twelve. The alcohols may be straight-chain or branched-chain and may contain inert substituents such as halo- and aryl-. Illustrative examples are methanol, ethanol, isopropanol, n-propanol, butanols, hexanols, 5-chloro-1-hexanol, 3-fluoro-1-propanol, 12-phenyl-1-dodecanol and the like.

The catalyst composition used in the instant process are used in typical fashion, for example, in packed beds, in batch reactors, or in fluidized beds. Reaction temperatures typically range from about 150° C. to about 500° C. Different alcohols have different optimum reaction temperatures which can readily be determined by routine experimentation. For methanol, a desirable reaction temperature is from about 200°–550° C., preferably from about 250°–450° C. and for 1,4-butanediol from about 150°–500° C., preferably from about 150°–300° C. The reaction product is subjected to standard separation techniques and product ethers are separated from unreacted alcohols. Unreacted materials may be conveniently recycled. Suitable inert solvents may also be utilized in the instant process such as for example alphatic compounds. Excess starting materials can be utilized for their solvent effects. Reaction pressures are not critical and they may be atmospheric, superatmospheric or subatmospheric.

The preparation of the compositions used as catalysts in the process of the instant invention and their utilization as catalysts will be further described below by the following illustrative embodiments which are provided for illustration and are not to be construed as limiting the invention.

ILLUSTRATIVE EMBODIMENTS

Composition Preparation

A porous silica gel (Davison Grade 57, surface area of 300 m²/g, pore volume of 1.0 cc/gm and density of 0.4 gm/cc) 20-30 mesh was pretreated in dry nitrogen at 700° C. for one-half an hour. Exposure of the dried support to air was avoided. In a glove box with a dry nitrogen atmosphere 5 grams of the dried support was impregnated with a solution prepared by dissolving 0.4 grams of $AlH_3.1/3(Et_2O)$ in 8 ml of tetrahydrofuran. The impregnated material was placed in a vycor tube and dry nitrogen passed over the catalyst as the temperature was increased in 50° C. intervals (15 min. at each temp.) to 700° C. and held at this temperature for 15 minutes. The finished composition was cooled with a nitrogen flow of 40 ml/min.

Similar compositions were prepared using high surface area silica gels (e.g. Davison Grade 03, surface area of 750 m²/g, pore volume of 0.43 gm/cc and density of 0.7 g/cc).

Similar compositions were made by activating at 500° to 550° C.

Conversion of Alcohols to Ethers

A catalyst according to this invention prepared as described above (3.8% wt. added aluminum; Davison Grade 57, 20-30 mesh; activated at 700° C.) was tested for activity in converting alcohols to ethers. Fourteen milliliters of catalyst was used in a vycor tube reactor.

1,4-Butanediol was pumped through the reactor at a LHSV of 2 cocurrent with a nitrogen flow of 40 ml/minute at atmospheric pressure. At 200° C. conversion of the alcohol to tetrahydrofuran was found to be 13.7% wt. When the LHSV was lowered to 1, the conversion to tetrahydrofuran increased to 35.1% wt. At 250° C. the conversion to tetrahydrofuran was substantially 100%.

Methanol was pumped through the reactor at a flow of 1 LHSV cocurrent with a nitrogen flow of 40 ml/minute. Product analysis showed that at 250° C., 300° C., and 350° C. conversion of methanol to dimethyl ether was 7, 33 and 65 percent by weight, respectively.

It can be seen from above that different alcohols have different reaction temperatures. For methanol, a desirable reaction temperature is from about 200°–550° C., preferably from about 250°–450° C. and for 1,4-butandiol from about 150°–500° C., preferably from about 150°–300° C.

I claim:

1. A process for converting alkanols to ethers which comprises contacting the alcohols at about 150° C. to about 550° C. with a catalyst prepared by a process which comprises impregnating a substantially dehydrated amorphorous silica gel with aluminum hydride dissolved in an anhydrous, nonhydroxyl containing organic solvent, drying the impregnated silica to remove the solvent and subsequently heating the impregnated silica at a temperature of about 300° to about 900° C. in a non-oxidizing atmosphere.

2. The process of claim 1 where in preparing the catalyst the impregnated silica is subsequently heated to a temperature of about 450° C. to about 750° C.

3. The process of claim 1 where in preparing the catalyst the impregnated silica before heating contains from about 0.01 to about 35 percent by weight of aluminum hydride measured as aluminum metal.

4. The process of claim 1 where in preparing the catalyst the impregnated silica before heating contains from about 0.1 to about 25 percent by weight of aluminum hydride measured as the metal.

5. The process of claim 1 where in preparing the catalyst the impregnated silica before heating contains from about 1 to about 10 percent by weight of aluminum hydride measured as the metal.

6. The process of claim 5 where in preparing the catalyst the aluminum hydride is $AlH_3 \cdot 1/3(CH_3CH_2)_2O$ dissolved in tetrahydrofuran or diethyl ether.

7. The process of claim 2 where in preparing the catalyst the impregnated silica before heating contains from about 0.01 to about 35 percent by weight of aluminum hydride measured as the metal.

8. The process of claim 2 where in preparing the catalyst the impregnated silica before heating contains from about 0.1 to about 25 percent by weight of aluminum hydride measured as the metal.

9. The process of claim 2 where in preparing the catalyst the impregnated silica before heating contains from about 1 to about 10 percent by weight of aluminum hydride measured as the metal.

10. The process of claim 9 where in preparing the catalyst the aluminum hydride is $AlH_3 \cdot 1/3(CH_3CH_2)_2O$ dissolved in tetrahydrofuran or diethyl ether.

11. The process of claim 1 wherein the alkanol is methanol and the temperature ranges from about 200° C. to about 550° C.

12. The process of claim 11 wherein the temperature ranges from about 250° C. to about 450° C.

13. The process of claim 1 wherein the alkanol is 1,4-butanediol and the temperature ranges from about 150° C. to about 500° C.

14. The process of claim 13 wherein the temperature ranges from about 150° C. to about 300° C.

* * * * *